(12) United States Patent
Smith

(10) Patent No.: US 11,806,459 B2
(45) Date of Patent: Nov. 7, 2023

(54) TARGETED APHERESIS TO TREAT PREECLAMPSIA

(71) Applicant: Henry J. Smith, Temecula, CA (US)

(72) Inventor: Henry J. Smith, Temecula, CA (US)

( * ) Notice: Subject to any disclaimer, the term of this patent is extended or adjusted under 35 U.S.C. 154(b) by 324 days.

(21) Appl. No.: 17/006,875

(22) Filed: Jan. 16, 2021

(65) Prior Publication Data
US 2022/0233755 A1    Jul. 28, 2022

(51) Int. Cl.
| | | |
|---|---|---|
| *A61M 1/36* | (2006.01) | |
| *A61M 1/34* | (2006.01) | |
| *A61K 31/727* | (2006.01) | |
| *A61P 9/12* | (2006.01) | |
| *G01N 33/68* | (2006.01) | |
| *B01D 61/14* | (2006.01) | |
| *B01D 69/02* | (2006.01) | |
| *B01D 15/38* | (2006.01) | |

(52) U.S. Cl.
CPC .......... *A61M 1/362* (2014.02); *A61K 31/727* (2013.01); *A61M 1/3496* (2013.01); *A61P 9/12* (2018.01); *B01D 15/3809* (2013.01); *B01D 61/145* (2013.01); *B01D 69/02* (2013.01); *G01N 33/689* (2013.01); *A61M 2202/07* (2013.01); *G01N 2333/475* (2013.01); *G01N 2800/368* (2013.01); *G01N 2800/56* (2013.01)

(58) Field of Classification Search
CPC ................ A61M 1/362; A61M 1/3496; A61M 2202/07; A61P 9/12; A61K 31/727; B01D 15/3809; B01D 61/145; B01D 69/02; G01N 33/689; G01N 2333/475; G01N 2800/368; G01N 2800/56
USPC ............................................................ 514/56
See application file for complete search history.

(56) References Cited

U.S. PATENT DOCUMENTS

| | | | |
|---|---|---|---|
| 8,979,787 B2 * | 3/2015 | Smith | A61M 1/3472 604/6.01 |
| 2023/0056992 A1 * | 2/2023 | Joo | A61P 9/12 |

* cited by examiner

*Primary Examiner* — Yih-Horng Shiao
(74) *Attorney, Agent, or Firm* — Camran V Parast

(57) ABSTRACT

This invention teaches a targeted apheresis method of treating a pregnant woman with preeclampsia, or who is predisposed to developing preeclampsia, utilizing immobilized binding agents contained within an apheresis device to remove sVEGFR-1 and sVEGFR-2, and one or more other harmful factors associated with preeclampsia selected from a list that includes: sEndoglin, Endothelin-1, TNF, IL-1, IL-6, IL-12, IL-18, digitalis-like factor, ouabain-like factor, marinobufagenin, .marinobufotoxenin, and telocinobufagin. The binding agents used are antibodies or aptamers or binding peptides. Reducing the concentration of sVEGFR-1, sVEGFR-2 and other harmful factors in the pregnant woman's blood using targeted apheresis will alleviate or delay the symptoms of preeclampsia, and thus postpone premature delivery of the baby so that the baby is born at term or as close to term as possible.

11 Claims, 5 Drawing Sheets

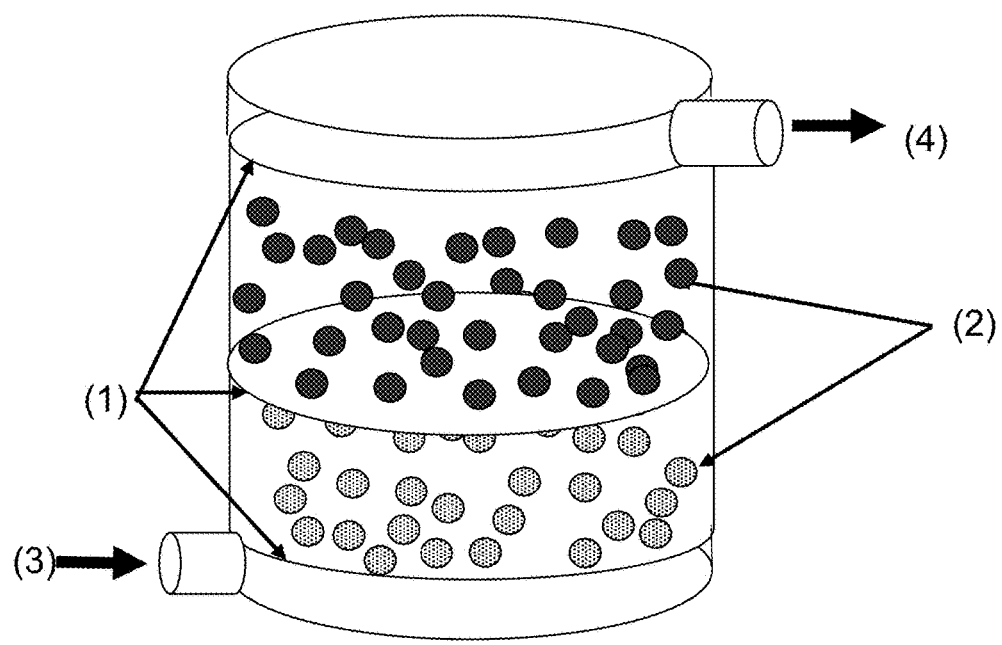
Figure 1. The Multi-Compartment Apheresis Device as disclosed in Claim 1. A first binding agent (e.g. anti-sVEGFR-1/sVEGFR-2 antibody) coated beads is shown in ◉. A second binding agent (e.g. anti-sEndoglin antibody) coated beads is shown in ●. Only a few beads that are highly magnified are shown for illustration.

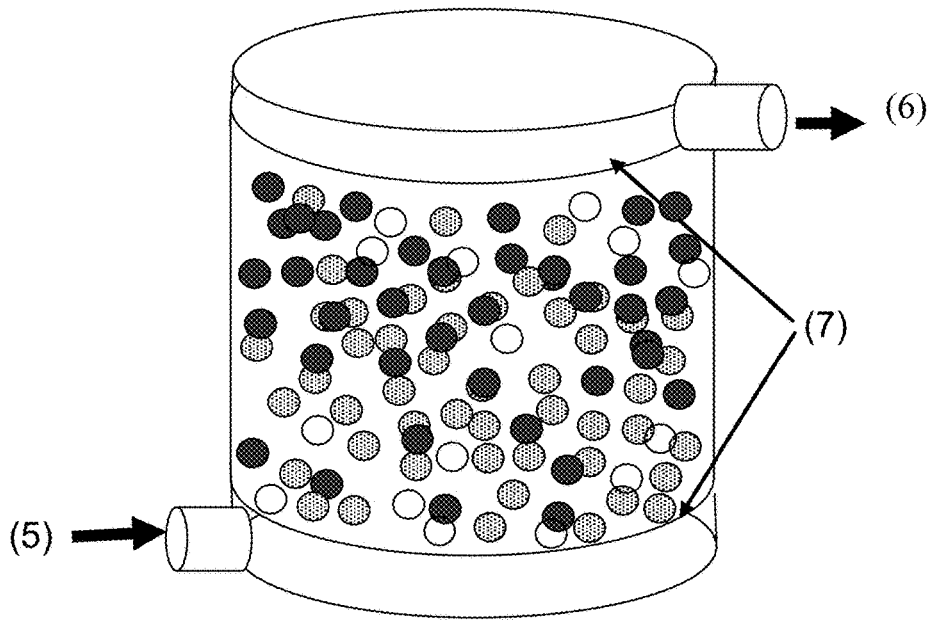

Figure 2. The Single Compartment Apheresis Device with different batches of beads as disclosed in Example 2. . A first binding agent (e.g. anti-sVEGFR-1/sVEGFR-2 antibody) coated beads is shown in ○. A second binding agent (e.g. anti-sEndoglin antibody) coated beads is shown in ◉. A third binding agent (e.g. anti-TNF antibody) coated beads is shown in ●. Only a few beads that are highly magnified are shown for illustration.

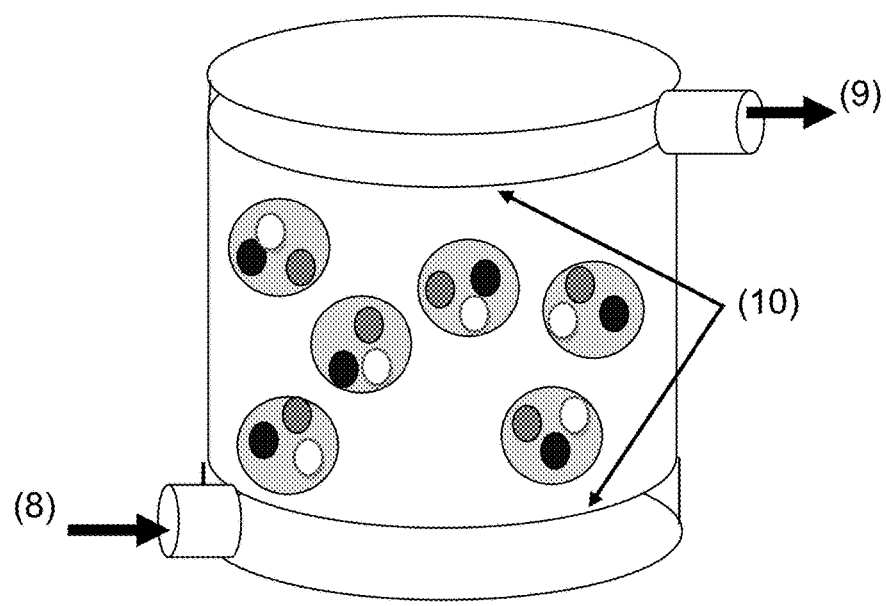
Figure 3. The Single Compartment Apheresis Device with single batch of beads as disclosed in Example 3. Each bead is coated with an anti-sVEGFR-1/sVEGFR-2 antibody (shown in black), plus an anti-Endoglin antibody (shown in white), plus an anti-TNF antibody (shown in grey). Only a few beads that are highly magnified are shown for illustration.

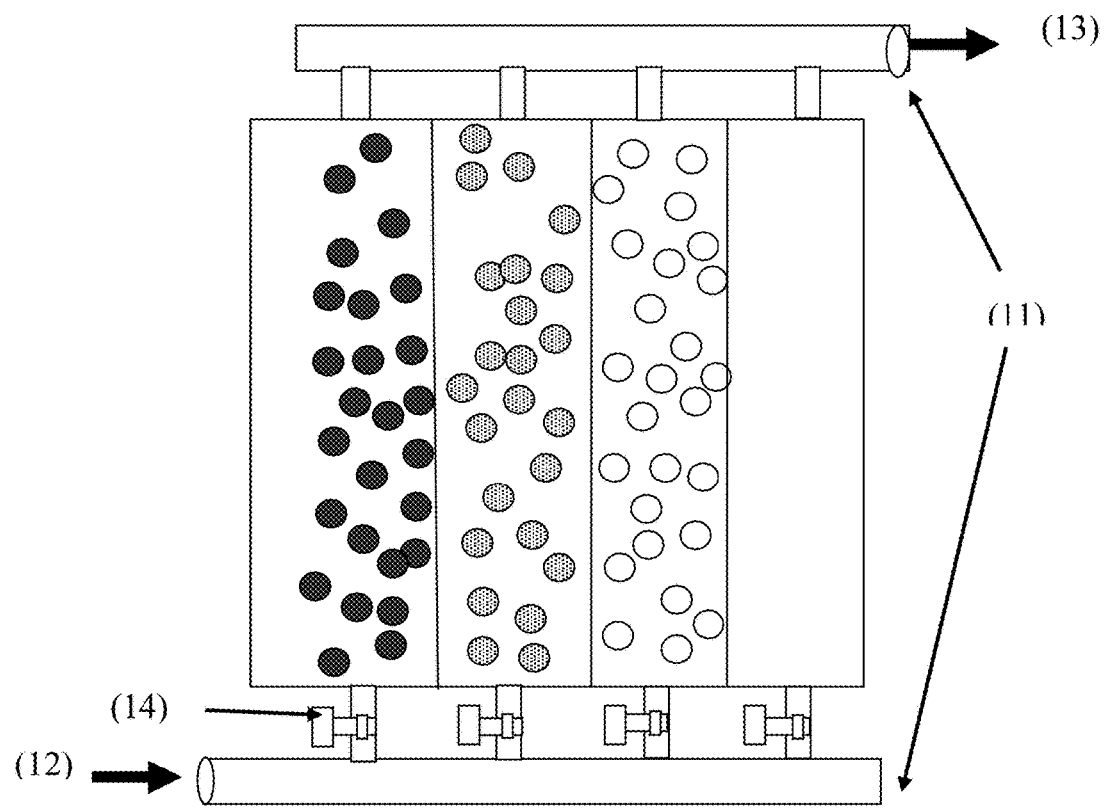

Figure 4. The Parallel Multi-Compartment Apheresis Device as disclosed in Example 4. Each compartment contains a different binding agent. For example a first compartment contains anti-sVEGFR-1/sVEGFR-2 antibody coated beads (shown in black); a second compartment contains anti-sEndoglin antibody coated beads (shown in grey); a third compartment contains anti-TNF antibody coated beads (shown in white). Only a few beads that are highly magnified are shown for illustration.

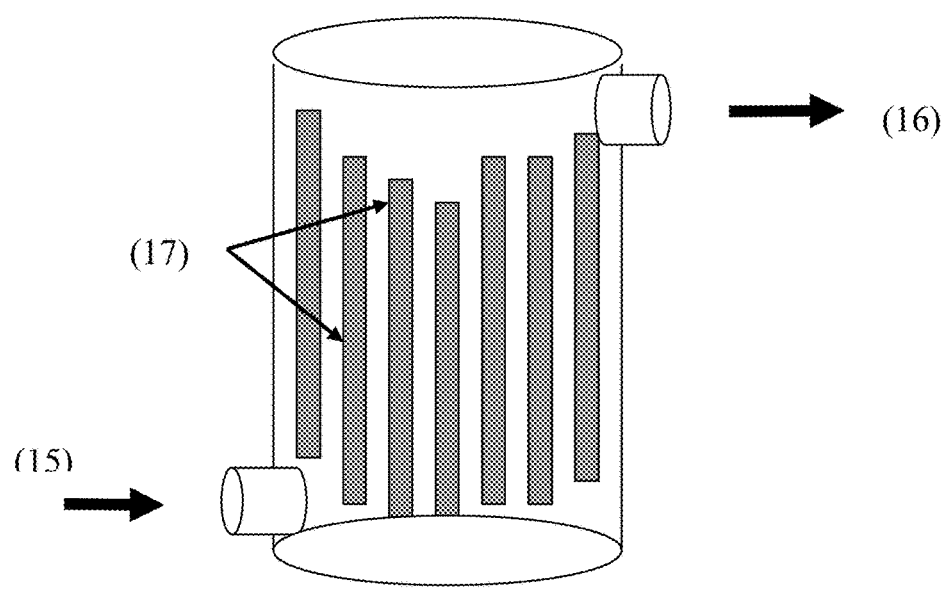
Figure 5. The Apheresis Device with Membrane disclosed in Example 5. An anti-sVEGFR-1/sVEGFR-2 binding agent (e.g. anti-sVEGFR-1/sVEGFR-2 antibody), plus one or more other binding agents (e.g. antibodies) to other harmful factors, are covalently attached to the membrane.

TARGETED APHERESIS TO TREAT PREECLAMPSIA

CROSS REFERENCE TO RELATED APPLICATIONS

This patent application claims priority to Provisional Patent Application No. 62/973,376 titled "Apheresis to Treat Preeclampsia" filed Oct. 2, 2019; and to Provisional Patent Application No. 62/974,703 titled "Targeted Apheresis to remove harmful factors associated with Preeclampsia". filed Dec. 19, 2019.

STATEMENT RE: FEDERALLY SPONSORED RESEARCH/DEVELOPMENT

Not Applicable

BACKGROUND TO THE INVENTION

Preeclampsia or toxemia during pregnancy is one of the leading causes of maternal and infant mortality. The symptoms of preeclampsia typically appear after the 20th week of pregnancy and are characterized by high blood pressure, edema and protein in the urine. In severe cases there is a massive rise in blood pressure that can result in severe complications, premature delivery of the baby and death of the mother or baby.

Preeclampsia can vary in severity from mild to life threatening. The mild form of preeclampsia is usually treated with bed rest and frequent monitoring. For moderate to severe cases, hospitalization is recommended and the patient is treated with blood pressure medication or anticonvulsant medications to prevent seizures. If the condition becomes life threatening to the mother or the baby labor is induced and the baby is delivered pre-term. Very pre-term babies have a high risk of dying, or being mentally and physically disadvantaged for life.

Preeclampsia is a complex multi-factorial disease with many factors associated with the disease. One particular growth factor—Vascular Endothelial Growth Factor-A (VEGF-A) appears to play a major role in the development of the placenta to support the growing baby. VEGF-A is an endothelial cell-specific mitogen, an angiogenic inducer, and a mediator of vascular permeability. VEGF-A binds as a homodimer to the homologous tyrosine kinase receptors Vascular Endothelial Growth Factor Receptor-1 (VEGFR-1) also known as the fms-like tyrosine kinase receptor (Flt-1); and Vascular Endothelial Growth Factor Receptor-2 (VEGFR-2) also known as the kinase domain receptor (KDR). It is hypothesized that too much VEGF-A binding to VEGFR-2 will result in the overdevelopment of an abnormal placental vasculature; while too little VEGF-A binding to VEGFR-2 will result in a poorly developed placental vasculature. Further that there are regulatory mechanisms to control the concentration of VEGF-A available to bind to VEGFR-2 and thus regulate normal placental development. One control mechanism appears to be mediated by VEGFR-1, which by binding to VEGF-A will reduce the amount of VEGF-A available to bind to VEGFR-2.

In addition to the growth receptors VEGFR-1 and VEGFR-2 present on cells, the same growth receptors are also found circulating in the blood. These soluble receptors sVEGFR-1 (aka sFlt-1) and sVEGFR-2 (aka sKDR) are also able to bind to VEGF-A and thus reduce the amount of circulating VEGF-A available to bind to the cellular growth receptors and consequently this would lead to poor placental development.

In addition to VEGF-A and the VEGFR-1 and VEGFR-2 system of controls there is also another circulating growth factor—Placental Growth Factor (PlGF) that appears to play a major role in placental development. Placental growth factor (PlGF) is a VEGF family member that is capable of inducing proliferation, migration, and activation of endothelial cells. PlGF binds as a homodimer to VEGFR-1 on trophoblast cells. PlGF however does not bind to VEGFR-2. It was observed that women with a normal pregnancy had high levels of circulating PlGF and low levels of sVEGFR-1; whereas women with preeclampsia had low levels of PlGF and high levels of sVEGFR-1. The level of sVEGFR-2 appeared to remain relatively unchanged throughout pregnancy in women with preeclampsia and in women with a normal pregnancy. It appeared that the high level of circulating sVEGFR-1 was binding out VEGF-A and PlGF, and that sVEGFR-2 was also contributing to binding out VEGF-A. The reduction in the levels of VEGF-A and PlGF was associated with developing the clinical symptoms of preeclampsia.

This invention teaches that reducing the level of circulating sVEGFR-1 and sVEGFR-2 in the mother's blood using targeted apheresis would alleviate the symptoms of preeclampsia and delay the premature delivery of the baby. The art is silent on the removal of both sVEGFR-1 and sVEGFR-2 using targeted apheresis as a means of treatment for pregnant women with preeclampsia, or who are predisposed to developing preeclampsia.

The rational for removing both sVEGFR-1 and sVRGFR-2 is that while the level of sVEGFR-1 increases markedly in preeclampsia and is the main component for sequestering VEGF-A, the level of sVEGFR-2 still represents a significant component for also sequestering VEGF-A. For example, although different studies have reported different levels of circulating sVEGFR-1 and sVEGFR-2 there is general agreement on a rough estimation of the total amount of each present in the circulation, and the relative amounts of each one to the other. For purposes of illustration, the median level of sVEGFR-1 prior to the onset of preeclampsia is about 1-3 ng/ml and increases to a median level of about 40 ng/ml when preeclampsia occurs. The level of sVEGFR-2 by comparison remains fairly constant at about 10 ng/ml before and during the course of preeclampsia. On average sVEGFR-2 represents about 20 percent of the circulating soluble receptors able to sequester VEGF-A in women with preeclampsia. Therefore removing sVEGFR-2 in addition to removing sVEGFR-1 will allow more VEGF-A to be bioavailable to promote normal placental development.

Another clinical indication where removal of sVEGFR-2 is important is in those women who are predisposed to develop preeclampsia but have not yet presented with the clinical symptoms of the disease. There is ongoing research into developing tests to identify these women in the hope that early detection and intervention could prevent or delay the development of preeclampsia. As noted above the level of sVEGFR-2 prior to the onset of preeclampsia is about three to ten times higher than the level of sVEGFR-1. Removal of sVEGFR-2 in addition to removing sVEGFR-1 using targeted apheresis in this group of pregnant women prior to the onset of preeclampsia may prevent or delay development of preeclampsia.

There are also other harmful factors in the mother's blood that are associated with preeclampsia. These include sEndoglin, Endothelin-1, and proinflammatory cytokines such as Tumor Necrosis Factor-alpha (TNF), interleukin-1 beta (IL-1), Interleukin-6 (IL-6), Interleukin 12 (IL-12), and Interleukin-18 (IL-18). Other factors that are implicated in preeclampsia are the tyrosine kinase inhibitors such as: endogenous digitalis-like factor, ouabain-like factor, marinobufagenin, .marinobufotoxenin, and telocinobufagin. Removal of one or more of these factors using targeted apheresis in addition to removing sVEGFR-1 and sVEGFR-2 may further ameliorate or delay the development of preeclampsia. The art is silent on the removal of sVEGFR-1, sVEGFR-2, and one or more additional harmful factors associated with preeclampsia using targeted apheresis to treat pregnant women with preeclampsia, or who are predisposed to developing preeclampsia, as a means to ameliorate or delay the development of preeclampsia.

Endoglin is a coreceptor for transforming growth factor β1 and β3 (TGF-β1 and TGF-β3, respectively), is highly expressed on cell membranes of vascular endothelium and syncytiotrophoblasts. Endoglin, as well as other TGF-β signaling components, is essential during angiogenesis. Patients with preeclampsia have elevated levels of soluble Endoglin (sEndoglin). The s-Endoglin is believed to act as a "physiologic sink" to down regulate TGF-beta signaling by binding to TGF-beta and preventing it from binding to the cellular receptors in the vasculature. This reduction in cellular signaling results in impaired vasodilation and decreased formation of blood capillaries in the placenta. Reducing the level of sEndoglin in addition to removing sVEGFR-1 and sVEGFR-2 may ameliorate or delay the symptoms of preeclampsia.

Another factor that appears to play a role in preeclampsia is Endothelin-1. Endothelins are a class of peptides synthesized by many tissues. One member of the group is Endothelin-1 which is an extremely powerful vasoconstrictor. Endothelin-1 is produced in the walls of blood vessels by endothelial and smooth muscle cells. It binds to the ETA receptors on other smooth muscle cells causing them to contract. This results in vasoconstriction and an increase in blood pressure. Women with preeclampsia have elevated levels of Endothelin-1 in the blood which may be one of the factors causing the high blood pressure associated with preeclampsia. Reducing the level of circulating Endothelin-1 in addition to removing sVEGFR-1 and sVEGFR-2 may result in lowering of the blood pressure.

The "sodium pump" is a universal cell surface enzyme called Na/K ATPase which maintains ion gradients between cells and the extracellular fluid. Inhibition of the activity of the sodium pump is associated with many disorders including hypertension and cardiovascular disease, diabetes and metabolic disorders, and preeclampsia and fetal abnormalities. The extracellular domain of this enzyme contains a highly conserved binding site, a receptor for a plant derived family of compounds—the digitalis glycosides. These compounds inhibit the Na/K ATPase enzyme and are used in the treatment of congestive heart failure and certain cardiac arrhythmias. This has led to speculation that endogenous digitalis-like factors (EDLF) might exist and play a role in hypertension and cardiac disorders. A number of interesting endogenous digitalis-like factors (EDLF) isolated from various human and animal tissues have been reported as having the capacity to bind to the digitalis receptor site. These include ouabain; marinobufagenin; marinobufotoxogenin, and telocinobufagin. Increased levels of EDLF have been found in patients with preeclampsia. Reducing the level of EDLF in addition to removing sVEGFR-1 and sVEGFR-2 may ameliorate or delay the symptoms of preeclampsia.

There are also other reports that other substances such as circulating pro-inflammatory factors may participate in the symptoms of preeclampsia. For example, there are reports that cytokines such as tumor necrosis factor alpha (TNF) and IL-1 markedly elevated Monocyte Chemoattractant Protein-1 (MCP-1) mRNA and protein levels in decidual cell monolayers in the trophoblast. This leads to enhanced decidual MCP-1 production and the consequent influx and activation of macrophages. The release of TNF by the latter would recruit additional macrophages and cause direct toxic effects on the endovascular trophoblast. The resultant hypoxia would sustain local overexpression of TNF contributing to maternal systemic endothelial cell activation, and this in turn would lead to preeclampsia. Reducing the level of proinflammatory cytokines such as tumor necrosis factor alpha (TNF), interleukin-1 (IL-1), interleukin 6 (IL-6), interleukin 12 (IL-12), and interleukin 18 (IL-18) in addition to removing sVEGFR-1 and sVEGFR-2 may ameliorate or delay the symptoms of preeclampsia.

"Targeted Apheresis" is a process whereby harmful substances in the blood are bound out by immobilized binding agents wherein each binding agent targets and binds out a specific harmful factor before the treated blood is returned to the patient. Typically, the blood from the preeclampsia patient is first separated into the plasma fraction and the cellular fraction using differential centrifugation or membrane filtration. The plasma fraction is then pumped through an apheresis device where the harmful factors are bound out by the immobilized binding agents. Typically, the binding agent. is an antibody that targets a specific harmful factor to be removed, and it is immobilized by covalently attaching it to an insoluble support matrix such as cross-linked agarose beads. The treated plasma is then remixed with the cellular blood elements and returned to the patient.

It is well-known in the art that there are other compounds such as aptamers and binding peptides that can target and bind to antigens in the same manner as antibodies. They can therefore be used as binding agents in lieu of antibodies in the targeted apheresis device. In this invention the term "binding agent" will refer to the antibodies or aptamers or binding peptides that can target and bind to sVEGFR-1 and/or sVEGFR-2, and to one or more of the other harmful factors associated with preeclampsia.

As noted above there are many factors that appear to be associated with preeclampsia. Removing one or more of these harmful factors using targeted apheresis in addition to removing sVEGFR-1 and sVEGFR-2 may provide additional benefit in the treatment of preeclampsia. The art is silent on a targeted apheresis method of treating a pregnant woman with preeclampsia, or who is predisposed to developing preeclampsia, by removing sVEGFR-1, sVEGFR-2, and one or more additional harmful factors selected from a list that includes: sEndoglin, Endothelin-1, TNF, IL-1, IL-6, IL-12, IL-18, digitalis-like factor, ouabain-like factor, marinobufagenin, .marinobufotoxenin, and telocinobufagin.

SUMMARY OF THE INVENTION

This invention teaches a targeted apheresis method of treating a pregnant woman with preeclampsia, or who is predisposed to developing preeclampsia, utilizing immobilized binding agents contained within an apheresis device to remove sVEGFR-1 and sVEGFR-2, and one or more other harmful factors associated with preeclampsia selected from a list that includes: sEndoglin, Endothelin-1, TNF, IL-1, IL-6, IL-12, IL-18, digitalis-like factor, ouabain-like factor, marinobufagenin, .marinobufotoxenin, and telocinobufagin.

The binding agents used are antibodies or aptamers or binding peptides. Reducing the concentration of sVEGFR-1 and sVEGFR-2, and other harmful factors as well in the pregnant woman's blood using targeted apheresis will alleviate or delay the symptoms of preeclampsia, and thus delay premature delivery of the baby so that the baby is born at term or as close to term as possible.

DESCRIPTION OF THE INVENTION

The circulating growth factors and their soluble receptors exist in dynamic equilibrium in the blood of the woman with preeclampsia. This includes PlGF, VEGF-A, sVEGFR-1; sVEGFR-2; PlGF bound to sVEGFR-1 (PLGF/sVEGFR-1 complex); VEGF-A bound to sVEGFR-1 (VEGF-A/sVEGFR-1 complex), and VEGF-A bound to sVEGFR-2 (VEGF-A/sVEGFR-2 complex). The levels of each will vary during the course of a normal pregnancy but there are abnormal changes in these levels when the woman develops preeclampsia.

This invention teaches the removal of VEGFR-1 and VEGFR-2 using targeted apheresis as a means of treating preeclampsia. Also the removal of one or more other harmful factors associated with preeclampsia may provide additional medical benefit. The following examples are provided for illustration only and are not to be construed as a limitation. This invention teaches the various modifications that can be made to the basic design of the apheresis device and the binding agents used, in order to improve the efficiency of the apheresis process. Those of skill in the art will be able to make various modifications and changes based on the teachings in this invention. Said changes are therefore considered to lie within the spirit and scope of this invention.

Example 1. Multi-Compartment Apheresis Device

In this example (FIG. 1) the apheresis device comprises two or more interconnected compartments separated by porous membranes (1). Within each compartment there is a binding agent attached to an insoluble supporting matrix such as cross-linked agarose beads (2). Only a few beads that are highly magnified are shown for illustration. The porous retaining membranes have pores that will retain the coated beads within each compartment while still allowing the plasma to flow through. The device has an inlet port (3) to allow plasma to enter the device and an outlet port (4) for the plasma to exit. Typically the apheresis device is constructed of a rigid plastic material. Additional compartments may be added depending on the number of other harmful factors to be removed.

To illustrate the basic design and process of this invention the first compartment could contain an anti-VEGFR-1/sVEGFR-2 antibody (shown in grey), the second compartment could contain a binding agent that targets an additional harmful factor e.g. sEndoglin. (shown in black) Additional compartments containing additional binding agents may be added depending on the additional harmful factors to be removed. When plasma is flowed through the device the binding agent in the first compartment will bind out sVEGFR-1 and sVEGFR-2. The plasma then flows into the second compartment where the binding agent will bind out sEndoglin. The treated plasma is then remixed with the cellular blood elements and returned to the patient.

In one embodiment of this invention immobilized PlGF and immobilized VEGF-A are used as binding agents. When plasma is flowed through the apheresis device the circulating sVEGFR-1 that has an open receptor site will bind to Immobilized PLGF and to immobilized VEGF-A, while circulating sVEGFR-2 will bind to the immobilized VEGF-A. The treated plasma is then remixed with the cellular blood elements and returned to the patient.

Example 2. Single Compartment Apheresis Device with Different Batches of Beads

In one embodiment of this invention an apheresis device comprising a single compartment is used (FIG. 2). There is an inlet port (5) for plasma to enter and an outlet port (6) for the plasma to exit. In this example the apheresis device consists of a single compartment containing a mixture of different batches of different binding agent coated beads. Only a few beads that are highly magnified are shown for illustration. For example one batch of beads are coated with an anti-sVEGFR-1/sVEGFR-2 antibody (shown in white); another batch of beads are coated with an anti-sEndoglin antibody (shown in grey), and yet another batch of beads are coated with an anti-TNF antibody (shown in black). There is a porous membrane (7) at the top and another at the bottom of the device to contain the beads.

When plasma is flowed through the compartment each batch of beads coated with a different binding agent will bind out its specific targeted harmful factor and the treated plasma is then remixed with the cellular blood elements and returned to the patient.

Example 3. Single Compartment Apheresis Device with Single Batch of Beads

In one embodiment of this invention an apheresis device comprising a single compartment is used (FIG. 3). There is an inlet port (8) for plasma to enter and an outlet port (9) for the plasma to exit. The compartment contains a batch of beads wherein each bead is coated with a mixture of binding agents. For example each bead is coated with an anti-sVEGFR-1/sVEGFR-2 antibody (shown is black), plus an anti-Endoglin antibody (shown in white), plus an anti-TNF antibody (shown in grey). Only a few beads that are highly magnified are shown for illustration. There is a porous membrane (10) at the top and at the bottom of the device to contain the beads within the device.

When plasma is flowed through the device the anti-VEGFR1/2 antibody will remove sVEGFR-1 and sVEGFR-2; the anti-sEndoglin antibody will remove sEndoglin, and the anti-TNF antibody will remove TNF. The treated plasma is then remixed with the cellular blood elements and returned to the patient.

Example 4 Parallel Multi-Compartment Apheresis Device

In one embodiment of this invention the apheresis device consists of multiple compartments arranged in parallel such that the plasma flows separately through each compartment (FIG. 4.) There is a manifold (11) with an inlet port (12) for plasma to enter and an outlet port (13) for plasma to exit. Each inlet port has a tap (14) to allow or shut off the flow of plasma through that compartment. Each compartment contains a different binding agent immobilized on beads. Only a few beads that are highly magnified are shown for illustration. For example one compartment contains beads coated with anti-sVEGFR-1/sVEGFR-2 antibody (shown in black), another compartment contains beads coated with an antisEndoglin antibody (shown in grey), and another compartment contains beads coated with an anti-TNF antibody (shown in white).

When plasma is flowed through the different compartments of the device the anti-VEGFR-1/sVEGFR-2 antibody will remove sVEGFR-1 and sVEGFR-2; the anti-sEndoglin antibody will remove sEndoglin, and the anti-TNF antibody will remove TNF. In certain instances one or more of the compartments can be closed to prevent the binding agent in that compartment from removing a specific factor below a certain level considered to be normal. The treated plasma is then remixed with the cellular blood elements and returned to the patient.

Example 5 Apheresis Device with Membrane

In one embodiment of this invention the apheresis device comprises a chamber enclosing a membrane coated with an anti-svEGFR-1/sVEGFR-2 antibody and also one or more antibodies targeting one or more additional harmful factors (FIG. 5). The device has an inlet port for plasma to enter (15) and an outlet port (16) for the plasma to exit. The membrane may be pleated or folded to increase its surface area; or preferably it may be in the form of a microtubular membranes (17) such as those commonly used in conventional apheresis. In this invention the membrane has no filtering function but is used solely to provide a large surface area to which the binding agents can be attached.

When plasma is flowed across the membrane the anti-sVEGFR-1/sVEGFR-2 antibody will bind out sVEGFR-1 and sVEGFR-2, and the other antibodies targeting other harmful factors will bind these out as well. The treated plasma is then remixed with the cellular blood elements and returned to the patient.

Support Matrix

In this invention the support matrix to which the binding agents are attached could vary in form and chemical composition provided the matrix material is insoluble, non-toxic, and presents a large surface for attachment of the binding agent. There is a wide variety of support material that can be employed; including cross-linked agarose beads, latex beads, silica beads, polyacrylamide beads and the like. In one preferred embodiment of this invention cross-linked porous agarose beads are used, but other matrixes made be utilized in like manner and are considered to lie within the scope of this invention.

In one embodiment of this invention the support matrix is a membrane. There are a variety of membranes manufactured with different chemical and physical properties. For example, they are manufactured from a variety of materials including but not limited to: cellulose diacetate (Plasma-APOS); polypropylene (Fenwal CPS-10); polysulfone (Sulflux-FS); polymethylmethacrylate (Plasmax-PS05). They will vary in their density, membrane thickness, surface charge, and pore size. The arrangement of the membranes can be in the form of flat sheets or pleated sheets or as stacked microtubules enclosed within a chamber. In this invention the membrane is not used for filtration but only to provide a very large surface area to which the binding agents can be attached.

Binding Agents:

In the examples disclosed above the binding agents used to remove sVEGFR-1 and sVEGR-2 and other harmful factors associated with preeclampsia are typically antibodies. However it is well known in the art that there are other types of binding agents such as aptamers and binding peptides that mimic the action of an antibody and therefore may be used in like manner.

Antibody:

In this invention the term "antibody" will refer to an antibody that targets any one of the harmful factors associated with preeclampsia. The antibody may be polyclonal, monoclonal or a recombinant protein. It includes the whole antibody molecule or the binding fragments of the molecule.

Polyclonal antibodies are prepared by immunizing various species of animals against the factor. Typically, the animals used are rabbits, goats, sheep and horses but other animals can also be used. The antisera from immunized animals are treated to isolate and purify the antibodies using established methods including salt-fractionation, gel-filtration and affinity chromatography. These and other methods of purifying antibodies are known to those of skill in the art.

Monoclonal antibodies are typically produced using murine hybridoma technology. The monoclonal antibodies can be purified using standard down-stream processing techniques such as affinity binding to Protein A. These and other methods of developing and purifying monoclonal antibodies are known to those skilled in the art and are within the scope of this invention. Monoclonal antibodies are often "humanized" by replacing certain portions of the murine antibody with a human component in order to prevent the patient from developing an immune reaction to the mouse protein.

Recombinant antibodies are produced using genetic engineering technology. Typically a wide variety of antibody binding domains are expressed as membrane surface or viral coat proteins (phage display). The antibody binding domain that binds to the desired target (antigen) is then isolated along with the corresponding genes which can be sequenced and introduced into various expression hosts (e.g. bacterial, yeast or mammalian cells) and used to produce a high yield of antibodies. The recombinant antibodies can be purified using standard down-stream processing techniques such as His-tagging the antibodies and isolating them using immobilized metal affinity chromatography. These and other methods of developing and purifying recombinant antibodies are known to those skilled in the art and are within the scope of this invention.

There are many methods whereby proteins such as antibodies can be covalently attached to the support matrix. For example, agarose beads are activated using cyanogen bromide or N-hydroxysuccinimide and the antibody is incubated with the activated agarose to allow coupling to occur. The unconjugated material is removed by washing with buffer and the antibody bound agarose is placed within a compartment of the targeted apheresis device. There are many different methods of chemically coupling proteins to a variety of insoluble support matrixes. These matrix materials and methods of protein coupling are known to those skilled in the art and are within the scope of this invention.

Aptamer:

Aptamers are small (i.e. 40 to 100 bases), synthetic oligonucleotides. They may be composed as a single-stranded DNA chain (ssDNA) or a single-stranded RNA chain (ssRNA). Each aptamer has a unique configuration as a result of the composition of the nucleotide bases in the chain causing the molecule to fold in a particular manner. Because of their folded structure each aptamer will bind selectively to a particular epitope in a manner analogous to an antibody binding to its antigen. In order to improve stability against nucleases found in vivo the oligonucleotides comprising the aptamer may be modified to avoid nuclease attack. They may for example be synthesized as L-nucleotides instead of D-nucleotides and thus avoid degradation from nucleases present in blood.

Aptamers are usually synthesized from combinatorial oligonucleotide libraries using in vitro selection methods such as the Systematic Evolution of Ligands by Exponential Enrichment (SELEX). This is a technique used for isolating functional synthetic nucleic acids by the in vitro screening of large, random libraries of oligonucleotides using an iterative process of adsorption, recovery, and amplification of the oligonucleotide sequences. The iterative process is carried out under increasingly stringent conditions to achieve an aptamer of high affinity for a particular target ligand. Once the nucleotide sequence is identified increased quantities of that aptamer can be synthesized. Since the SELEX was first introduced a variety of other methods and variations of producing aptamers have been developed. These methods are known to those of skill in the art and are within the scope of this invention. In this invention the term "aptamer" will include all types and varieties of aptamers including single-strand DNA aptamers, single-strand RNA aptamers, branched aptamers and chemically modified aptamers There are many methods for covalently attaching an aptamer to the support matrix. For example, a 3'-amino modified group (3'-end-cap) is introduced that will allow coupling of the aptamer to N-hydroxysuccinimide activated cross-linked agarose beads. Any remaining unbound aptamers are removed by washing the beads with a suitable solution such as buffered saline and the aptamer conjugated beads are then placed within a compartment of the apheresis device. The methods of coupling aptamers to various insoluble support matrixes are known to those of skill in the art and are within the scope of this invention.

Binding Peptide:

Binding peptides are composed of a chain of aminoacids that are synthesized and selected to target a particular antigen. There are various methods for preparing synthetic or biological peptide libraries composed of up to a billion different sequences, and for identifying a particular peptide sequence that will target a particular epitope. Typically a large number of different peptide sequences are allowed to react with the target and the peptide with the highest binding affinity is isolated and sequenced. Once the binding peptide sequence is identified increased quantities of that binding peptide can be produced by synthesis or using genetic engineering technology. The means of producing synthetic or biologically derived peptides are known to those of skill in the art and are within the scope of this invention. In this invention the term "binding peptide" will include the whole peptide molecule or the active site on the peptide molecule capable of binding to its target antigen.

There are many methods for covalently attaching a peptide to the support matrix To facilitate conjugation the peptide is often produced with a chemical group at one end available for cross-linking to the activated support matrix. For example, agarose beads are activated using cyanogen bromide or N-hydroxysuccinimide and the peptide is incubated with the activated agarose to allow coupling to occur. The unconjugated material is removed by washing with buffer and the peptide coated beads are placed within a compartment of the targeted apheresis device. There are many different methods of chemically coupling peptides to a variety of insoluble support matrixes. These matrix materials and methods of peptide coupling are known to those skilled in the art and are within the scope of this invention.

In one embodiment of this invention the binding agent used to remove sVEGFR-1 is an anti-sVEGFR-1 antibody; and the binding agent to remove sVEGFR-2 is an anti-sVEGFR-2 antibody. In one further embodiment of this invention an antibody that can bind to common antigens present on sVEGFR-1 and sVEGFR-2 is used to remove both VEGFR-1 and sVEGFR-2. In this invention said antibody is termed as the anti-sVEGFR-1/sVEGFR-2 antibody.

In one embodiment of this invention the binding agent used to remove sVEGFR-1 is an anti-sVEGFR-1 aptamer; and the binding agent to remove sVEGFR-2 is an anti-sVEGFR-2 aptamer. In one further embodiment of this invention an aptamer that can bind to common antigens present on sVEGFR-1 and sVEGFR-2 is used to remove both sVEGFR-1 and sVEGFR-2. In this invention said aptamer is termed as the anti-sVEGFR-1/sVEGFR-2 aptamer.

In one embodiment of this invention the binding agent used to remove sVEGFR-1 is an anti-sVEGFR-1 binding peptide; and the binding agent to remove sVEGFR-2 is an anti-sVEGFR-2 binding peptide. In one further embodiment of this invention a binding peptide that can bind to common antigens present on sVEGFR-1 and sVEGFR-2 is used to remove both sVEGFR-1 and sVEGFR-2. In this invention said binding peptide is termed as the anti-sVEGFR-1/sVEGFR-2 binding peptide.

In this invention the term "targeted apheresis" is used to describe the extracorporeal removal of specific harmful substances associated with preeclampsia using immobilized binding agents that can target and remove each specific harmful substance without removing normal blood components.

In this invention the term "remove" does not mean complete removal of the harmful substance from the blood. It is well known that when the cleaned blood is returned to the patient during therapeutic apheresis there is always a residual level of the harmful substance remaining in the blood of the patient no matter how long or efficiently the apheresis treatment is performed. Generally as a rule of thumb there is approximately a 50% reduction in the blood level of the substance being removed for every 1.5 times the blood volume of the patient is processed during therapeutic apheresis.

In one embodiment of this invention whole blood from the patient with preeclampsia is processed by the apheresis devices disclosed in this invention. Those devices that utilize a membrane as the support matrix can be used without modification to also process blood as well as plasma. Those apheresis devices that use regular sized beads (i.e. 10-50 um diameter beads) as the support matrix however, will require some modification. Typically the beads used will be larger than 100 um in diameter, and preferably they could be up to 300 um or more in size. The upper and lower retaining membranes or sieves that contain the beads are also made to have pores that are smaller than the beads they have to retain e.g. a membrane pore size less than 100 um to retain the 100 um beads, and a membrane pore size less than 300 um to retain the 300 um beads. At the same time the membrane pore size must be large enough to allow the blood cells to pass through the membrane. For example when 100 um beads are used the membrane pore size could be 50-90 um which will allow all the components of whole blood to flow through while still retaining the 100 um beads within the device; or when 300 um beads are used the membrane pore size could be 100-250 um which will allow whole blood to flow through while still retaining the 300 um beads within the device.

When apheresis is performed the patient is treated with an anti-coagulant in order to prevent the extracorporeal blood or plasma from clotting during the procedure. Typically the anticoagulant used is either heparin or citrate. In one embodiment of this invention heparin is specified as the anti-coagulant to use because it also has a second function of markedly improving the efficient removal of sVEGFR-1. The rational for doing so is because in addition to the sVEGFR-1 circulating in the blood there is a major amount of sVEGFR-1 sequestered in tissues, which upon exposure to heparin is released into the blood circulation. The targeted apheresis process will now be able to remove a larger amount of sVEGFR-1 and thereby further extend the period of remission of preeclampsia.

This invention teaches that removing sVEGFR-1 and sVEGFR-2, and one or more other harmful factors using targeted apheresis would ameliorate the symptoms of preeclampsia and delay premature delivery of the baby. The duration of the beneficial effect of targeted apheresis however could be limited, and therefore it may be necessary to repeat the apheresis treatment multiple times in order to extend the period of remission so that the baby is born at term or as close to term as possible.

This invention also teaches that in addition to removing harmful factors associated with preeclampsia it may be beneficial to restore the level of VEGF-A and/or PlGF to their respective normal levels commensurate with the gestational age of the developing baby by administering supplemental amounts of VEGF-A and/or PlGF to the mother during pregnancy. Additional research and clinical trials will be needed to confirm the efficacy and safety of such treatment.

In order to diagnose and treat preeclampsia it is vital that the level of free VEGF-A and free PlGF be measured accurately. Unfortunately current methods for measuring free VEGF-A and free PlGF developed by different laboratories have given varying and sometimes conflicting results. This invention discloses several methods for isolating free VEGF-A and free PlGF from blood, or plasma, or serum samples. The isolated (free) VEGF-A and isolated (free) PlGF can now be measured using standard assay methods.

One method is to remove sVEGFR-1 and sVEGFR-2 using an affinity procedure. Briefly antibodies to sVEGFR-1 and sVEGFR-2 are conjugated to cross-linked agarose beads. When plasma or serum is mixed with the beads the sVEGFR-1 and sVEGFR-2 are bound out leaving the free VEGF-A and free PlGF in solution. After centrifugation to sediment the beads (or using magnetic separation) the free PlGF and free VEGF-A in the solution can be measured using an immunoassay procedure.

Another method is to use ultrafiltration to separate the free low molecular weight growth factors from the bound growth factors attached to high molecular weight sVEGFR-1 and sVEGFR-2. The ultrafiltration method uses a porous membrane that has a pore size that allows VEGF-A and PlGF to filter through, while retaining bound growth factors attached to sVEGFR-1 and sVEGFR-2. The filter unit consists of a vessel separated into two compartments by the ultrafiltration membrane. The blood or plasma or serum sample is placed in the upper chamber and a gravitational force is applied by centrifuging the unit so that low molecular weight substances (i.e. VEGF-A and PlGF) in solution can filter through and be collected in the lower chamber. These types of filtration units are commercially available either as single units (e.g. Millipore corporation) or in a microplate format where the base of each microwell comprises an ultrafiltration membrane (e.g. Pall corporation). Upon centrifuging the microplate the filtrate passes through the membrane and is collected into a second microplate sited below the first microplate.

Another method of accelerating the filtration process is to apply a vacuum to the lower chamber so that the solution carrying the low molecular weight substances are filtered through the membrane due to atmospheric pressure. For example using the same microplate format as that described above the microplate is placed in a manifold and a vacuum is applied to the lower chamber and the filtrate is collected into a second microplate sited below the first microplate. These types of microplate units are commercially available (e.g. Pall corporation).

The free VEGF-A and free PlGF can now be measured using conventional immunoassay methods. The following is an example of a conventional ELISA method that can be used to measure VEGF-A. Typically a capture antibody such as a monoclonal antibody to an epitope on VEGF-A is absorbed or covalently attached to the microwells of a microplate. A plasma or serum sample is added and incubated to allow any VEGF-A in the sample to become bound by the capture antibody. After washing to remove unbound material a second anti-VEGF-A antibody conjugated with horseradish peroxidase (HRPO) is added. The antibody is either a polyclonal antibody or a monoclonal antibody targeting an epitope on VEGF-A different from that targeted by the capture antibody. After an incubation period to allow the HRPO conjugated antibody to bind to any VEGF-A present the microwells are washed to remove any unbound HRPO antibody. A substrate solution such as tetramethylbenzidine (TMB) plus hydrogen peroxide is added. The colorless substrate will turn a blue color whose intensity is directly proportional to the amount of HRPO present and bound to the captured VEGF-A. The amount of VEGF-A in the sample is measured by comparison to a standard curve prepared using known amounts of VEGF-A.

Essentially the same ELISA method used to measure VEGF-A can be used to measure free PlGF: Typically a capture antibody such as a monoclonal antibody to an epitope on PlGF is absorbed or covalently attached to the microwells of a microplate. A plasma or serum sample is added and incubated to allow any PlGF in the sample to become bound by the capture antibody. After washing to remove unbound material a second anti-PlGF antibody conjugated with horseradish peroxidase (HRPO) is added. The antibody is either a polyclonal antibody or a monoclonal antibody targeting an epitope on PlGF different from that targeted by the capture antibody. After an incubation period to allow the HRPO conjugated antibody to bind to any PlGF present the microwells are washed to remove any unbound HRPO antibody. A substrate solution such as tetramethylbenzidine (TMB) plus hydrogen peroxide is added. The colorless substrate will turn a blue color whose intensity is directly proportional to the amount of HRPO present and bound to the captured PlGF. The amount of PlGF in the sample is measured by comparison to a standard curve prepared using known amounts of PlGF.

In some instances it may be helpful to compare the levels of free VEGF-A and free PlGF to the levels of sVEGFR-1 and sVEGFR-2 to determine if a ratiometric analysis of the results is a more sensitive or accurate means of diagnosing or monitoring the course of the disease. There are commercially available methods of measuring sVEGFR-1 and sVEGFR-2 that appear to be sufficiently accurate to be used. The level of sVEGFR-1 and sVEGFR-2 obtained using these assays can be compared to the level of free PlGF and free VEGF-A.

It will be obvious to one of skill in the art of immunoassays that there are many modifications that can be made based on the disclosures in this invention. For example: using a competitive type of assay instead of the sandwich type of assay, or using a different detection reagent (e.g. florescent label) or a different enzyme or substrate. Said modifications are considered to lie within the spirit and scope of this invention.

This invention discloses a novel method of targeted apheresis for treating a woman with preeclampsia, or who is predisposed to developing preeclampsia. It teaches that the removal of sVEGFR-1 and sVEGFR-2 and other harmful factors associated with preeclampsia using targeted apheresis will delay or alleviate the symptoms of the disease, and thus prevent or delay the premature delivery of the baby so that the baby is born at term or as close to term as possible. This invention also teaches a method of accurately measuring free VEGF-A and free PlGF in order to monitor the course of the disease. It will be apparent from the disclosures in this invention that there are many changes and modifications that can be made that lie within the spirit and scope of this invention. Such modifications and changes are therefore considered to lie within the scope of this invention.

REFERENCES

Adair et al. Digoxin Immune Fab Treatment for Severe Preeclampsia. Am. J. Perinatol. 2010; 27 (8): 455-662

Affinity Chromatography. Amersham Biosciences Handbook pp 1-151.

Bagrov et al. 1998. Characterization of a urinary bufadienolide Na+, K+ ATPase inhibitor in patients after acute myocardial infarction. Hypertension 31:1097-1103

Buckalew V. et al. Endogenous digitalis-like factors in hypertension In. Hypertension, Pathophysiology, Diagnosis and Management. Raven Oress. New York 1995 $2^{nd}$ edn pp 1055-1067.

Charnock-Jones et al., Determination of the Circulating Levels of the Soluble Form of the VEGF-R1 (sFlt-1) in Women at High Risk of Developing Preeclampsia. J. Soc. Gynecol. 2003

Clark B A, et al., Plasma endothelin levels in preeclampsia: elevation and correlation with uric acid levels and renal impairment. Am J Obstet Gynecol. 1992 March; 166(3): 962-968.

Clark et al. A Vascular Endothelial Growth Factor antagonist is produced by the human Placenta and Released into the maternal circulation. Biol. Reprod. 59:1540-1548 (1998).

Ellington A D & Szostak J W. In vitro selection of RNA molecules that bind specific ligands. Nature. 346:818-822 (1990).

Friedman S. A. et al Biochemical corroboration of endothelial involvement in severe preeclampsia. Am J Obstet Gynecol 172:202-203 (1995).

Geysen H. M. and Mason T. J. 1993. Bioorganic & Medicinal Chemistry Letters 3(3):397-404.

Graves S. and Williams G. Endogenous digitalis-like factors. Annu. Rev. Med. 1987; 38; 433-444

Halpin D. R. and Harbury P. B. DNA Display 1. Sequence Encoded Routing of DNA Populations. Published in the July 2004 Issue of PLoS Biology www.plosbiology.org Hung T H et al., Secretion of Tumor Necrosis Factor-α from Human Placental Tissues Induced by Hypoxia-Reoxygenation Causes Endothelial Cell Activation in Vitro. A Potential Mediator of the Inflammatory Response in Preeclampsia Am J Pathol. 2004 March; 164(3): 1049-1061.

Journal of Clinical Apheresis—Special Issue Volume 25. Clinical Applications of Therapeutic Apheresis: An Evidence Based Approach. $5^{th}$ Edition (2010). Karumanchi S. A. et al. Method of treating preeclampsia and eclampsia. U.S. Pat. No. 7,846,433

Kawamura A, et al. On the structure of endogenous ouabain. Proc Natl Acad Sci USA 1999; 96: 6654-6659

Lockwood, C J. et al. Regulation of Monocyte Chemoattractant Protein-1 Expression by Tumor Necrosis Factor-α and Interleukin-1β in First Trimester Human Decidual Cells Implications for Preeclampsia. Am J Pathol. 2006 February; 168(2): 445-452.

Lopatin et al. 1999. Circulation bufadienolide and cardenolide sodium pump inhibitors in preeclampsia. J. Hypertension. 17:1179-1187.

Maynard S. E. et al. Excess placental soluble fms-like tyrosine kinase 1 (sFlt-1) may contribute to endothelial dysfunction, hypertension, and proteinuria in preeclampsia. J Clin Invest. 111(5):649-658 (2003).

Myers J. E. et al. Evidence for multiple circulating factors in preeclampsia. Am J Obstet Gynecol 196:266.e1-266.e6 (2007)

Osol G. et al. Placental growth factor is a potent vasodilator of rat and human resistance arteries. Am J Physiol Heart Circ Physiol 294:H1381-H1387 (2008).

Smith H. et al. Treatment for Preeclampsia in Pregnant Women using Targeted Apheresis. U.S. Patent application 60/643,117 (2005).

Taylor R. N. et al. Women with preeclampsia have higher plasma endothelin levels than women with normal pregnancies. J Clin Endocrinol Metab 71:1675-1677 (1990).

Thadhani R. et al. Pilot Study of Extracorporeal Removal of soluble Fms-Like Tyrosine Kinase 1 in Preeclampsia. Circulation. Published online Aug. 1, (2011).

Tsatsaris et al., Overexpression of the Soluble Vascular Endothelial Growth Factor Receptor in Preeclamptic Patients: Pathophysiological Consequences, J Clin. Endocrinol. Metab. 88: 5555-5563 (2003).

Tuerk C & Gold L. Systematic evolution of ligands by exponential enrichment: RNA ligands to bacteriophage T4 DNA polymerase. Science. 249:505-510. (1990). Venkatesha. Soluble endoglin contributes to the pathogenesis of preeclampsia. Nat Med 12 (6): 642-9. (2006).

Wang Y, et al. Heparin-mediated extracorporeal low density lipoprotein precipitation as a possible therapeutic approach in preeclampsia. Transfus Apher Sci 35(2):103-10 (2006)

Weir F. J. et al. Does endothelin-1 reduce superior mesenteric artery blood flow velocity in preterm neonates? Arch Dis Child Fetal Neonatal Ed 80:F123-F127 (1999).

Zwick M. B. et al. Current Opinion in Biotechnology, 9(4):427-436 (1998).

What is claimed is:

1. A targeted apheresis method of treating a pregnant woman with preeclampsia, or who is predisposed to develop preeclampsia, wherein the pregnant woman's-blood or plasma is flowed through an apheresis device that contains a) immobilized binding agents that bind and target circulating vascular endothelial growth factor receptors (VEGFRs) selected from sVEGFR-1 and sVEGFR-2; and b) one or more other immobilized binding agents that bind one or more harmful factors selected from the group consisting of: sEndoglin, Endothelin-1, TNF, IL-1, IL-6, IL-12, IL-18, digitalis-like factor, ouabain-like factor, marinobufogenin, marinotoxigenin, and telocinobufagin.

2. The targeted apheresis method of treating a pregnant woman with preeclampsia, or who is predisposed to develop preeclampsia, according to claim 1, wherein the immobilized binding agents to remove sVEGFR-1 and sVEGFR-2 are either a) an anti-sVEGFR-1 antibody and an anti-sVEGFR-2 antibody or b) an anti-sVEGFR-1/sVEGFR-2 antibody; and wherein c) the other binding agents to remove the one or more harmful factors listed in step b) of claim 1 are specific antibodies each targeting the harmful factor.

3. The targeted apheresis method of treating a pregnant woman with preeclampsia, or who is predisposed to develop preeclampsia, according to claim 1, wherein the immobilized binding agents to remove sVEGFR-1 and sVEGFR-2 are either a) an anti-sVEGFR-1 aptamer and an anti-sVEGFR-2 aptamer or b) an anti-sVEGFR-1/sVEGFR-2 aptamer; and wherein c) the other binding agents to remove the one or more harmful factors listed in step b) of claim 1 are specific aptamers each targeting the harmful factor.

4. The targeted apheresis method of treating a pregnant woman with preeclampsia, or who is predisposed to develop preeclampsia, according to claim 1, wherein the immobilized binding agents to remove sVEGFR-1 and sVEGFR-2 are either a) an anti-sVEGFR-1 binding peptide and an anti-sVEGFR-2 binding peptide or b) an anti-sVEGFR-1/sVEGFR-2 binding peptide; and wherein c) the other binding agents to remove the one or more harmful factors listed in step b) of claim 1 are specific binding peptides each targeting the harmful factor.

5. The targeted apheresis method of treating a pregnant woman with preeclampsia, or who is predisposed to develop preeclampsia, according to claim 1, wherein the apheresis device is composed of multiple interconnecting chambers, with each chamber containing a different immobilized binding agent targeting the harmful factor associated with preeclampsia.

6. The targeted apheresis method of treating a pregnant woman with preeclampsia, or who is predisposed to develop preeclampsia, according to claim 1, wherein the apheresis device is composed of a single chamber containing a mixture of different batches of beads with each batch of beads coated with a different binding agent targeting the harmful factor associated with preeclampsia.

7. The targeted apheresis method of treating a pregnant woman with preeclampsia, or who is predisposed to develop preeclampsia, according to claim 1, wherein the apheresis device is composed of a single chamber containing a single batch of beads; and wherein each bead is coated with a mixture of different binding agents with each binding agent targeting the harmful factor associated with preeclampsia.

8. The targeted apheresis method of treating a pregnant woman with preeclampsia, or who is predisposed to develop preeclampsia, according to claim 1, wherein the apheresis device is composed of a single chamber containing a membrane coated with a mixture of binding agents with each binding agent targeting the harmful factor associated with preeclampsia.

9. The targeted apheresis method of treating a pregnant woman with preeclampsia, or who is predisposed to develop preeclampsia, according to claim 1, wherein the apheresis device is composed of a set of chambers arranged in parallel with each chamber containing a batch of beads, and with each batch of beads coated with a different binding agent targeting the harmful factor associated with preeclampsia.

10. The targeted apheresis method of treating a pregnant woman with preeclampsia, or who is predisposed to develop preeclampsia, according to claim 1, wherein the pregnant woman-is treated with heparin in order to release tissue sequestered sVEGFR-1 into the blood circulation so that the sVEGFR-1 can be removed using targeted apheresis.

11. The targeted apheresis method of treating a pregnant woman with preeclampsia, or who is predisposed to develop preeclampsia, according to claim 1, wherein the pregnant woman is treated with one or more targeted apheresis treatments in order to ameliorate or delay the symptoms of preeclampsia and thus delay premature delivery of the baby; so that the baby is born at term, or as close to term as possible.

* * * * *